United States Patent
Martz

(10) Patent No.: US 12,053,556 B2
(45) Date of Patent: Aug. 6, 2024

(54) SANITIZING DEVICE

(71) Applicant: Clean Light Laboratories LLC, Scottsdale, AZ (US)

(72) Inventor: Carrie Martz, Scottsdale, AZ (US)

(73) Assignee: Clean Light Laboratories, LLC, Scottsdale, AZ (US)

( * ) Notice: Subject to any disclaimer, the term of this patent is extended or adjusted under 35 U.S.C. 154(b) by 354 days.

(21) Appl. No.: 17/774,619

(22) PCT Filed: Nov. 6, 2019

(86) PCT No.: PCT/US2019/060125
§ 371 (c)(1),
(2) Date: May 5, 2022

(87) PCT Pub. No.: WO2021/091556
PCT Pub. Date: May 14, 2021

(65) Prior Publication Data
US 2022/0395598 A1    Dec. 15, 2022

(51) Int. Cl.
*A61L 2/10*    (2006.01)

(52) U.S. Cl.
CPC ............. *A61L 2/10* (2013.01); *A61L 2202/11* (2013.01); *A61L 2202/122* (2013.01); *A61L 2202/14* (2013.01)

(58) Field of Classification Search
CPC .. A61L 2/10; A61L 2202/11; A61L 2202/122; A61L 2202/14; A61L 2202/24; A61F 5/4553
USPC ..................................... 250/455.11
See application file for complete search history.

(56) References Cited

U.S. PATENT DOCUMENTS

| | | |
|---|---|---|
| 2013/0004367 A1 | 1/2013 | Roberts |
| 2013/0344454 A1* | 12/2013 | Nath .................... A61N 5/0613 607/90 |
| 2018/0010764 A1 | 1/2018 | Yoon |
| 2018/0055960 A1 | 3/2018 | Reiber et al. |
| 2018/0169280 A1 | 6/2018 | Stibich et al. |
| 2018/0264154 A1 | 9/2018 | Bettles et al. |
| 2018/0361001 A1 | 12/2018 | Liao et al. |
| 2021/0338863 A1* | 11/2021 | Hammad .................. A61L 2/10 |

FOREIGN PATENT DOCUMENTS

| | | |
|---|---|---|
| CN | 106880855 A | 6/2017 |
| KR | 101940092 B1 | 1/2018 |

OTHER PUBLICATIONS

International Search Report and Written Opinion from related application No. PCT/US2019/060125 mailed out on Jan. 30, 2020 (9 pages).

* cited by examiner

*Primary Examiner* — Kiet T Nguyen
(74) *Attorney, Agent, or Firm* — Zeman-Mullen & Ford, LLP

(57) ABSTRACT

A sanitizing device particularly suitable for sanitizing personal use items such as a menstrual cup. The sanitizing device includes top and bottom half members, top and bottom reflective members positioned within the top and bottom half members, respectively, and a planar quartz glass member to ensure that all interior and exterior surfaces of the menstrual cup are adequately exposed to UVC light to achieve sanitization.

19 Claims, 5 Drawing Sheets

SANITIZING DEVICE

FIELD OF INVENTION

The present invention is generally directed to a sanitizing device which includes a top member having a reflective inner surface, a bottom member having a reflective inner surface, at least one LED member positioned near the inner reflective reflector surface of the bottom member, a battery member for powering the LED member, and an activation button/switch for activating the LED member. The inner reflective surfaces may be comprised of polytetrafluoroethylene (PTFE). The present invention is also directed to a top member having a reflector member contained therein and a bottom member having a reflector member contained therein wherein the reflector members each comprise separate members apart from, and contained within, the top and bottom members, respectively. The reflector members may each comprise PTFE or a reflective PTFE coating contained on a surface of the top and bottom members. Due to its configuration, the sanitizing device of the present invention is particularly suitable for sanitizing menstrual cups.

BACKGROUND OF THE INVENTION

There are a number of systems and devices that utilize LED technology for sanitizing and disinfecting products or items that are routinely used by people. For example, there are a number of device containing LEDS for sanitizing personal items such as phones, keyboards, other personal electronic items, cosmetic tools, hygiene devices, adult toys, children's toys, personal medical tools and devices, etc.

Menstrual cups are hygiene devices that have been known and in use for some time. Traditional menstrual cups are designed for multiple reuses and must be cleaned before reuse. Menstrual cups are typically cleaned by washing them with a mild soap and water to prevent decomposition of the material that is used to make the cup. Non-oil, pH balanced, plant-based cleansers are often recommended. Some manufacturers even recommend immersing the menstrual cup in boiling water to clean and disinfect the cup between periods of nonuse. However, often times appropriate cleansers or other means for cleaning the cup may not be available. Accordingly, there is a need for a reliable and effective sanitizing device for menstrual cups.

The sanitizing device of the present invention which utilizes UV-C LEDs and reflective PTFE is particularly suitable and effective for sanitizing and disinfecting menstrual cups. When utilized to sanitize and disinfect menstrual cups, the present invention prolongs the life of the menstrual cup while ensuring the vaginal health of the user.

SUMMARY OF THE INVENTION

The present invention is directed to a sanitizing device, which is particularly suitable for sanitizing a menstrual cup, which includes an outer shell member having a top half and a bottom half, a top reflector member positioned within the top half of the outer shell member and a bottom reflector positioned within the bottom half of the outer shell member wherein the top and bottom reflector members each comprise PTFE, at least one LED member positioned within the bottom reflector member, a battery member in communication with the LED member(s) and positioned within the bottom half of the outer shell member below the bottom reflector member, and an activation button or switch for activating the LED member(s). The sanitizing device may further include a USB-C connector positioned within the bottom half of the outer shell member below the bottom reflector member and in communication with the battery member for charging the battery member. The sanitizing device may also include a quartz glass member positioned within the bottom reflector member above the LED member(s) for supporting a personal use item, such as a menstrual cup, during sanitization. The quartz glass member may have a planar configuration that extends across an entire interior diameter of the bottom reflector member. The planar quartz glass member may be supported in a position within the bottom reflector member above the LED member(s) with the aid of support members that extend outward from an inner circumference of the bottom reflector member.

An interior of the top reflective member may have a tapered configuration such that it forms a generally cone like shape and the top half of the outer shell member which contains the top reflective member may have a dome like shape. The sanitizing device may also include a light member, such as an LED, that is visible from an outer surface of the bottom half of the shell member which indicates whether the LED member(s) positioned within the bottom reflector member are in activated state.

The sanitizing device may further include a magnet and a sensor that works in conjunction with the magnet to detect if the top and bottom halves of the outer shell member are in a closed and secured or sealed configuration. The sensor may function to prevent the sanitizing device from being activated unless the top and bottom halves of the outer shell member are in the closed and secured/sealed position.

The LED member(s) contained within the bottom reflector member may be in communication with, or contained on, a printed circuit board and the LED member(s) may comprise UV-C LED members. Further, the LED member(s) may comprise a plurality of LED members positioned about an interior circumference of the bottom reflector member and at least one LED member positioned near a center of the bottom reflective member.

In another exemplary embodiment, the sanitizing device of the present invention may include a bottom member having a cup like shape and a top member having a dome like shape that fits on top of the bottom member to form an outer shell, a top reflector member positioned within the top member and a bottom reflector member positioned within the bottom member where a surface of each of the top and bottom reflector members is covered with a PTFE coating, a printed circuit board containing a plurality of LED members positioned within the bottom reflector member, a quartz glass member positioned within the bottom reflector member above the printed circuit board, a battery positioned within the bottom member and in communication with the printed circuit board for powering the circuit board and LED members, and an activation button or switch for activating the LED members. The quartz glass member may have a planar configuration that extends across an entire interior diameter of the bottom reflector member so that it can support a personal use item to be sanitized, such as a menstrual cup. The planar quartz glass member may be supported in a position within the bottom reflector member above the LED member(s) with the aid of support members that extend outward from an inner circumference of the bottom reflector member.

This exemplary embodiment of the sanitizing device may also include a locking member for securing the bottom member to the top member as well as a magnet and sensor that work in conjunction with one another to detect if the top and bottom members are in a secured/sealed configuration with one another. The sensor may function to prevent the sanitizing device from being activated unless the top and bottom members are in a secured/sealed configuration with one another. Further, an interior of the top reflector member may be tapered to form a generally cone like shape that enables a personal use item such as a menstrual cup to be contained within it while sanitizing the menstrual cup.

The plurality of LED members may comprise UV-C LED members. Further, the plurality of LED members may comprise five UV-C LED members evenly positioned about an interior circumference of the bottom reflector member and two UV-C LED members positioned near a center of the bottom reflective member. In addition, the sanitizing device may further include a USB-C connector positioned within the bottom member below the bottom reflector member for charging the battery and an LED process indicator visible from an outside surface of the bottom member which shows when the sanitizing device is operating.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

DESCRIPTION OF EXEMPLARY EMBODIMENTS

Figure 2:
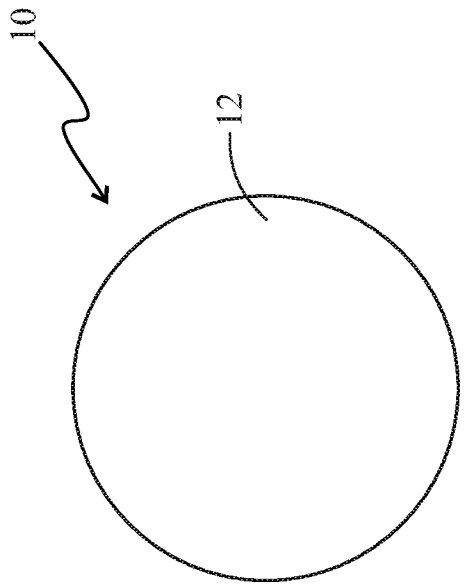
FIG. 2 is a top view of the exemplary embodiment of the sanitizing device shown in FIG. 1.

In the following detailed description of exemplary embodiments, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made a part of this disclosure.

Figure 3:
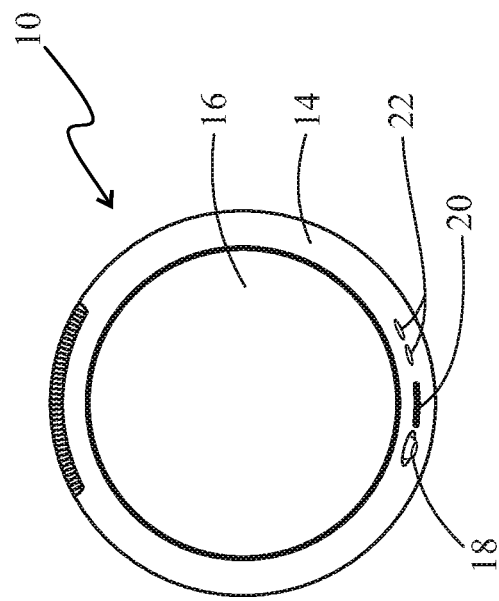
FIG. 3 is a bottom view of the exemplary embodiment of the sanitizing device shown in FIG. 1.
Figure 1:
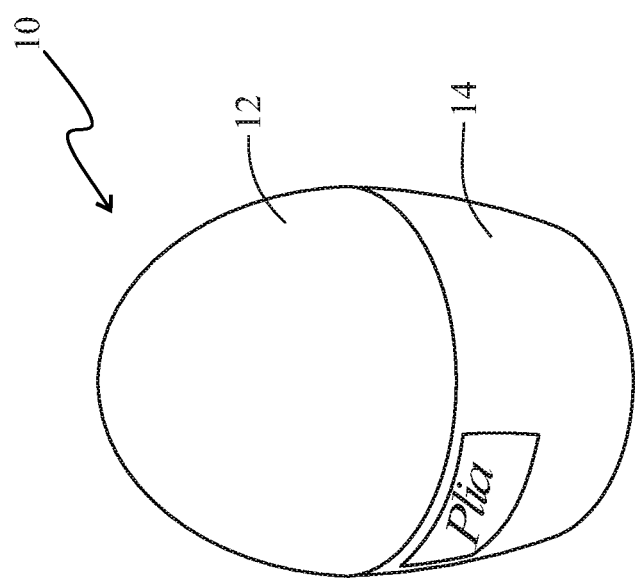
FIG. 1 is a perspective view of an exemplary embodiment of a sanitizing device in accordance with the present invention.
Figure 4:
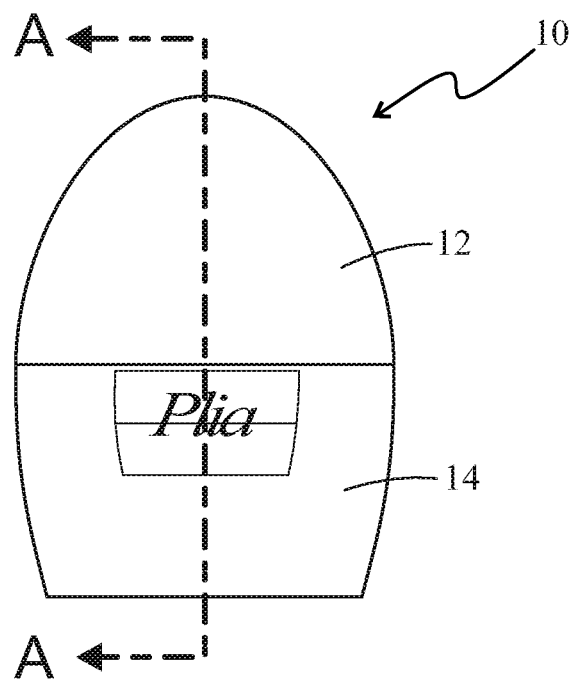
FIG. 4 is a front view of the exemplary embodiment of the sanitizing device shown in FIG. 1.

The present invention is directed to a sanitizing device. Although the sanitizing device of the present invention is particularly suitable for sanitizing menstrual cups, it may be used to sterilize and/or disinfect other personal use items. An outer perspective view of one exemplary embodiment of the sterilizing device 10 of the present invention is shown in FIG. 1. Sterilizing device 10 includes an outer shell having a top half member 12 and a bottom half member 14. The bottom half member 14 may have a cup like shape and the top half member 12 may have a dome like shape (or half an egg like shape) that fits on top of the bottom half member 14. The top half member 12 and bottom half member 14 may be connected and/or secured to one another by way of a twist open locking mechanism, a number of which are well known in the art for connecting members together to enable easy access to an inside of the connecting members. As shown in FIGS. 1 and 4, the height of top half member 12 may be slightly greater than the height of bottom half member 14. A top plan view of the sanitizing device 10 shown in FIG. 1 is presented in FIG. 2 and a bottom plan view of the sanitizing device 10 shown in FIG. 1 is presented in FIG. 3. In the top plan view presented in FIG. 2, only the top half member 12 can be seen while in the bottom plan view presented in FIG. 3, the bottom 16 of bottom half member 14 can be seen along with an activation button or switch 18, a USB charging port connection 20, and a light indicator(s) 22, such as LEDS, which indicate whether the sanitizing device 10 is in an activated state, all of which are positioned within or on an outer surface of bottom half member 14. Top half and bottom half members 12, 14 of the outer shell are preferably comprised of a hard, durable polymer or plastic material such as, for example, acrylonitrile butadiene styrene (ABS).

Figure 5:
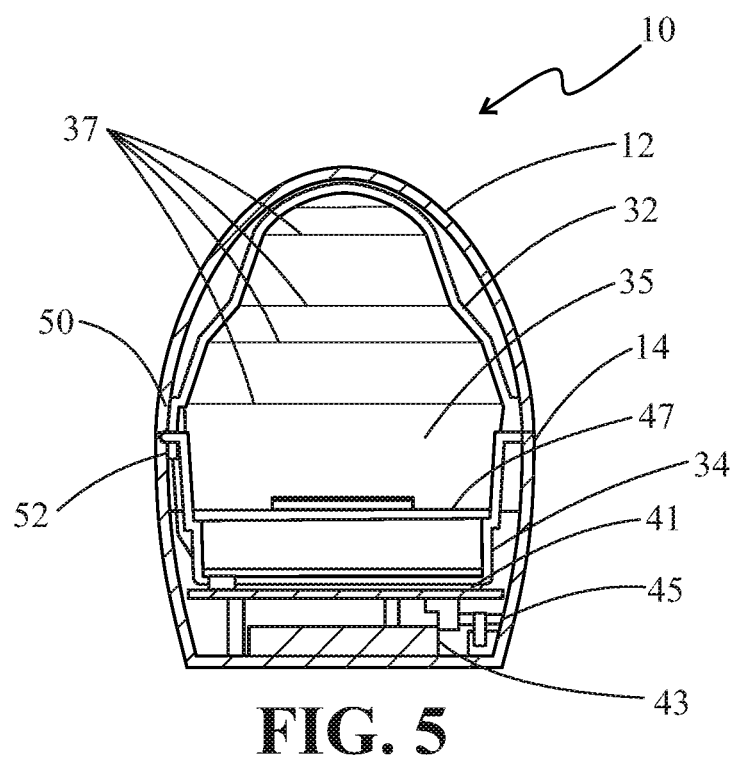
FIG. 5 is a cross-sectional view of the interior of the exemplary embodiment of the sanitizing device shown in FIG. 4 taken along line A-A.

FIG. 4 is a front view of the exemplary embodiment of the sanitizing device 10 shown in FIG. 1 having top and bottom half members 12, 14. A cross-sectional view of the interior of the exemplary embodiment of the sanitizing device 10 shown in FIG. 4 taken along line A-A is presented in FIG. 5. As shown in FIG. 5, a top reflector member 32 is positioned/contained within top half member 12 and a bottom reflector member 34 is positioned/contained within bottom half member 14. Top and bottom reflector members 32, 34 may be completely comprised of polytetrafluoroethylene (PTFE) or expanded polytetrafluorethylene (e-PTFE) or alternatively, they may each be comprised of a different material that is coated with a PTFE or e-PTFE layer such that the PTFE or e-PTFE layer faces toward the interior opening 35 contained within the sanitizing device 10 for housing the personal care item, such as a menstrual cup (See FIG. 10), that is being sanitized. Lines 37 shown in FIG. 5 represent the gradual interior tapering of the top reflector member 32.

Ultraviolet (UV) disinfection/sanitization relies on radiation emitted in the wavelength range of 250 nm-280 nm (UVC) to inactivate pathogens. PTFE and e-PTFE materials provide more than 95% reflectance of UVC light making them ideal materials for the top and bottom reflector members 32, 34 of the sanitizing device 10 to ensure that personal use items, such as menstrual cups, are fully and completely disinfected/sanitized. Sanitizing device 10 includes one or more LED members 39 (See FIG. 7) contained within the bottom reflector member 34, which may be further contained on a printed circuit board 41. Sanitizing device 10 also includes a battery 43 and a USB charging port 45 in communication with the battery for charging the battery 43. The LED member(s) 39 may be UV-C LED members, the charging port connector 45 may be a USB-C connector, and the battery 43 may be a lithium ion battery. When the battery powers the printed circuit board 41 and the LED light(s) 39 are activated, the top and bottom reflector members 32, 34 function to reflect the UVC light from the LED light(s) 39 so that it reaches all surfaces of a personal care item, such as a menstrual cup, to sanitize/disinfect all surfaces of the personal care item/menstrual cup.

As further shown in FIG. 5, sanitizing device 10 may also include a quartz glass member 47 positioned within the bottom reflector member 34 and elevated above the LED light member(s) 39 or the printed circuit board 41 containing the LED light member(s) 39. The personal use item to be sanitized, such as a menstrual cup, is positioned on the quartz glass member 47 contained within the bottom reflector member 34 so that the UVC light generated by the LED light member(s) 39 can be thoroughly moved around the interior of the personal care item (such as the menstrual cup) to ensure that all interior surfaces of the personal care item (menstrual cup) are sanitized/disinfected. The quartz glass member 47 may have a planar configuration that extends across an entire interior diameter of the bottom reflector member 34 so that it can support a personal use item to be sanitized, such as a menstrual cup. The planar quartz glass member 47 may be supported in a position within the bottom reflector member 34 above the LED member(s) 39 or the printed circuit board 41 containing the LED light member(s) 39 with the aid of support members that extend outward from an inner circumference of the bottom reflector member 34.

The sanitizing device 10 may also include a magnet 50 and a sensor 52 that works in conjunction with the magnet 50 to detect if the top and bottom half members 12, 14 of the outer shell member are in a closed and secured/sealed configuration. The sensor 52 may be a Hall effect sensor and may function to prevent the sanitizing device 10 from being activated unless the top and bottom half members 12, 14 of the outer shell are in the closed and secured/sealed position. This is a safety function of sanitizing device 10 to prevent operation of the device 10 when the device 10 is not in a closed and secured/sealed configuration.

Figure 6:
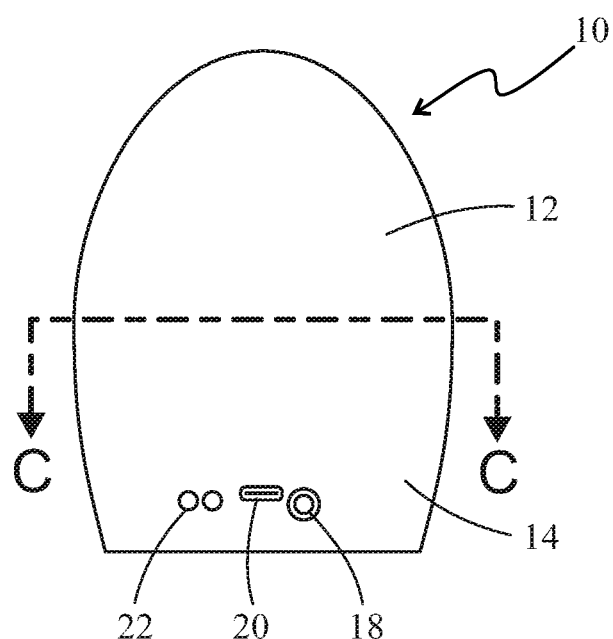
FIG. 6 is a rear view of the exemplary embodiment of the sanitizing device shown in FIG. 1.
Figure 7:
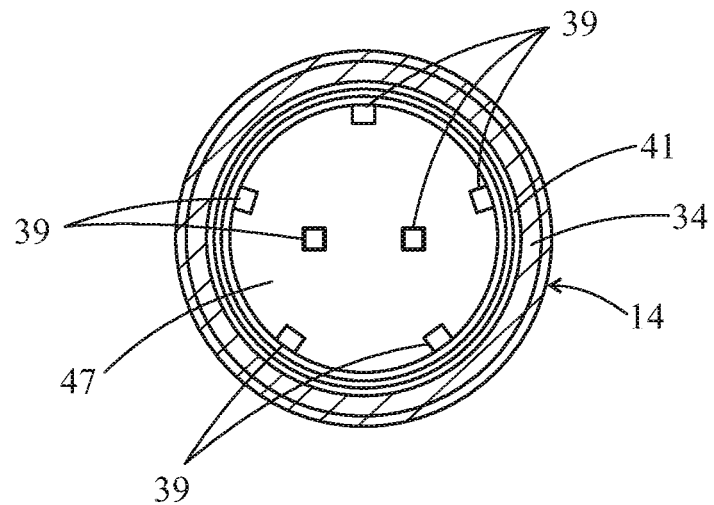
FIG. 7 is a cross-sectional view of the bottom interior of the exemplary embodiment of the sanitizing device shown in FIG. 6 taken along line C-C.

FIG. 6 is a rear view of the exemplary embodiment of the sanitizing device 10 shown in FIG. 1. Bottom half member 14 of sanitizing device 10 includes activation button or switch 18, USB charging port connection 20, and light indicator(s) 22, such as LEDS, which indicate whether the sanitizing device 10 is in an activated state, all of which are positioned within or on an outer surface of bottom half member 14. FIG. 7 is a cross-sectional view of the bottom interior of the exemplary embodiment of the sanitizing device shown in FIG. 6 taken along line C-C. As shown in FIG. 7, bottom reflector member 34 is contained within bottom half member 14. Quartz glass member 47 is also contained within bottom reflector member 34 and positioned above the LED member(s) 39 or the printed circuit board 41 containing the LED light member(s) 39. LED members 39 may comprise UV-C LED members. Further, the plurality of LED members 39 may comprise five UV-C LED members evenly positioned about an interior circumference of the bottom reflector member 34 and two UV-C LED members positioned near a center of the bottom reflective member 34.

Figure 8:
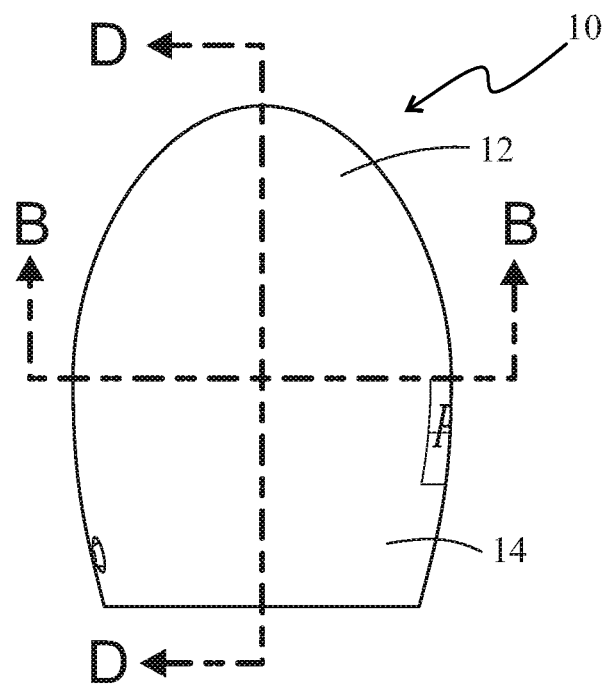
FIG. 8 is a side view of the exemplary embodiment of the sanitizing device shown in FIG. 1.
Figure 9:
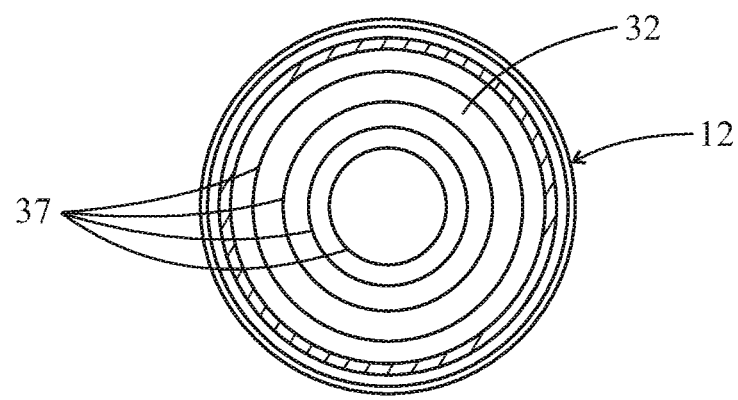
FIG. 9 is a cross-sectional view of the top interior of the exemplary embodiment of the sanitizing device shown in FIG. 8 taken along line B-B.

FIG. 8 is a side view of the exemplary embodiment of the sanitizing device 10 shown in FIG. 1. FIG. 9 is a cross-sectional view of the top interior of the exemplary embodiment of the sanitizing device 10 shown in FIG. 8 taken along line B-B. As shown in FIG. 8, top reflector member 32 is contained within top half member 14. Lines 37 represent the gradual interior tapering of the top reflector member 32. The interior of top reflector member 32 is tapered in stages (reflected by lines 37) to accommodate the shape of a personal use item, such as a menstrual cup, and more importantly, to ensure that adequate UVC light is reflected within the sanitizing device 10 to ensure that all surfaces of the personal use item such as the menstrual cup is exposed to the UVC light and thus sanitized/disinfected. The combination of the quartz glass member 47 contained in the bottom reflector member 34 and the tapered shape of the top reflector member 32 ensure that all interior and exterior surfaces of the personal use item, such as the menstrual cup, are adequately exposed to UVC light to ensure that all surfaces are sanitized/disinfected.

Figure 10:
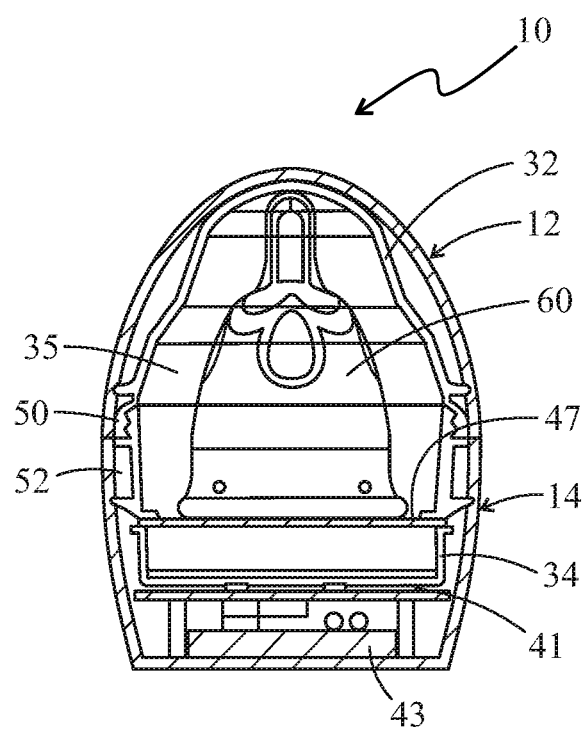
FIG. 10 is a cross-sectional view taken along line D-D of the interior of the exemplary embodiment of the sanitizing device shown in FIG. 8 with a menstrual cup positioned inside the device.

A cross-sectional view taken along line D-D of the interior of the exemplary embodiment of the sanitizing device shown in FIG. 8 with a menstrual cup 60 positioned inside the device is presented in FIG. 10. As shown in FIG. 10, the menstrual cup 60 is positioned on the quartz glass member 47 contained in the bottom reflector member 34. The menstrual cup 60 extends into the interior of the top reflective member 32. When the sanitizing device 10 is activated via activation button or switch 18, LED light members 39 produce UVC light that is projected up into the interior of menstrual cup 60 and onto the exterior surfaces of menstrual cup 60. Top and bottom reflective members 32, 34 further reflect UVC light produced by LED light members 39 into, on, and all around menstrual cup 60 to ensure that all surfaces of menstrual cup 60 are exposed to UVC light and thus sanitized/disinfected. The UV-C LED members positioned within the bottom reflective member used in combination with the PTFE or e-PTFE of the top and bottom reflector members, along with the quartz glass member, provide a sanitizing device with extensive reflective properties to ensure complete and effective sanitization while at the same time providing a sterilizing device that is easy to clean and reuse.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A sanitizing device comprising:
an outer shell member having a top half and a bottom half;
a top reflector member positioned within the top half of the outer shell member wherein an interior of the top reflector member is tapered to form a generally cone like shape and a bottom reflector member positioned within the bottom half of the outer shell member;
at least one LED member positioned within the bottom reflector member;
a quartz glass member positioned within the bottom reflector member above said at least one LED member;
a battery member in communication with said at least one LED member and positioned within the bottom half of the outer shell member below the bottom reflector member; and
an activation button or switch for activating said at least one LED member.

2. The sanitizing device of claim 1 further comprising a USB connector in communication with the battery member and positioned within the bottom half of the outer shell member below the bottom reflector member for charging the battery member.

3. The sanitizing device of claim 1 further comprising a light member visible from an outer surface of the bottom half of the shell member which indicates whether said at least one LED member positioned within the bottom reflector member is in an activated state.

4. The sanitizing device of claim 1 wherein the top half of the outer shell member comprises a circular dome like shape.

5. The sanitizing device of claim 1 further comprising a magnet and a sensor that works in conjunction with the magnet to detect if the top and bottom halves of the outer shell member are in a closed and secured or sealed configuration.

6. The sanitizing device of claim 5 wherein the device cannot be activated unless the sensor detects that the top and bottom halves of the outer shell are in a closed and secured/sealed position.

7. The sanitizing device of claim 1 wherein said at least one LED member comprises a UV-C LED.

8. The sanitizing device of claim 1 wherein a bottom of the bottom reflector member is circular and said at least one LED member comprises a plurality of LED members positioned evenly about an interior circumference of the bottom reflector member and at least one LED member is positioned near a center of the bottom reflective member.

9. The sanitizing device of claim 1 wherein said at least one LED member is contained on a printed circuit board that is positioned within the bottom reflector member.

10. The sanitizing device of claim 1 wherein the tapering of the interior of the top reflector member is non-uniform.

11. A sanitizing device comprising:
a bottom member having a cup like shape and a top member having a dome like shape that fits on top of the bottom member;
a top reflector member positioned within the top member wherein an interior of the top reflector member is tapered to form a generally cone like shape and a bottom reflector member positioned within the bottom member;
a printed circuit board containing a plurality of LED members positioned within the bottom reflector member;
a quartz glass member positioned within the bottom reflector member above the printed circuit board;
a battery positioned within the bottom member and in communication with the printed circuit board for powering the circuit board and LED members; and
an activation button or switch for activating the LED members.

12. The sanitizing device of claim 11 further comprising a locking member for securing the bottom member to the top member.

13. The sanitizing device of claim 12 further comprising a magnet and a sensor that works in conjunction with the magnet to detect if the top and bottom members are in a secured/sealed configuration with one another.

14. The sanitizing device of claim 13 wherein the device cannot be activated unless the sensor detects that the top and bottom members are in a secured or sealed configuration with one another.

15. The sanitizing device of claim 11 further comprising a USB connector positioned within the bottom member below the bottom reflector member for charging the battery.

16. The sanitizing device of claim 11 further comprising an LED process indicator visible from an outer surface of the bottom member which shows when the sanitizing device is operating.

17. The sanitizing device of claim 11 wherein each of the plurality of LED members comprise a UV-C LED member.

18. The sanitizing device of claim 17 wherein the plurality of UV-C LED members comprise five UV-C LED members evenly positioned about an interior circular circumference of the bottom reflector member and two UV-C LED members positioned near a center of the bottom reflective member.

19. The sanitizing device of claim 11 wherein the tapering of the interior of the top reflector member is non-uniform.

* * * * *